(12) United States Patent
Pitts et al.

(10) Patent No.: US 9,250,190 B2
(45) Date of Patent: *Feb. 2, 2016

(54) REAGENT AND METHOD USING THE SAME

(71) Applicant: JPP Chromatography Limited, Plymouth, Devon (GB)

(72) Inventors: Leslie John Pitts, Devon (GB); Michael Gerard Pallot, Devon (GB); Phillip Jones, Plymouth (GB)

(73) Assignee: JPP Chromatography Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/086,236

(22) Filed: Nov. 21, 2013

(65) Prior Publication Data

US 2014/0141519 A1    May 22, 2014

(30) Foreign Application Priority Data

Nov. 21, 2012 (GB) .................................. 1220902.9

(51) Int. Cl.
*G01N 21/78* (2006.01)
*G01N 33/68* (2006.01)

(52) U.S. Cl.
CPC ............ *G01N 21/78* (2013.01); *G01N 33/6806* (2013.01); *Y10T 436/10* (2015.01); *Y10T 436/108331* (2015.01); *Y10T 436/17* (2015.01); *Y10T 436/200833* (2015.01)

(58) Field of Classification Search
CPC ....... G01N 21/77; G01N 21/78; G01N 33/68; G01N 33/6806; Y10T 436/10; Y10T 436/107497; Y10T 436/108331; Y10T 436/143333; Y10T 436/17; Y10T 436/200833; Y10T 436/201666; Y10T 436/202499; Y10T 436/25
USPC ............. 436/8, 17, 18, 86, 89, 9, 4, 128, 129, 436/130, 164, 166, 174, 147, 106; 252/408.1; 422/82.05, 82.09, 82.12
See application file for complete search history.

(56) References Cited

U.S. PATENT DOCUMENTS

| 3,435,064 A | * | 3/1969 | Cinnamon et al. ............... 560/51 |
| 3,778,230 A | * | 12/1973 | Arikawa et al. ................. 436/43 |
| 3,918,907 A | | 11/1975 | Stephens |
| 4,274,833 A | | 6/1981 | Pickering |

FOREIGN PATENT DOCUMENTS

| CN | 102618621 A | 8/2012 |
| GB | 1349491 A | 4/1974 |
| SU | 1597700 A1 | 10/1990 |
| WO | 2008081959 A1 | 7/2008 |

OTHER PUBLICATIONS

Lie, S. Abstract from Mitteilungen der Versuchsstation fuer das Gaerungsgewerbe in Wien, vol. 26(9), 1972.*
Spackman, Darrel H., et al., Automatic Recording Apparatus for Use in the Chromatography of Amino Acids, The Rockefeller Institute for Medical Research, New York 21, NY, Analytical Chemistry, vol. 30, No. 7, Jul. 1958, pp. 1190-1206.
WPI abstract accession No. 2012N8235779, [retrieved on Oct. 3, 2013].
Bhushan, R., et al., Direct thin layer chromatography enantioresolution of some basic DL-amino acids using a pharmaceutical industry waste as chiral impregnating reagent, Journal of Pharmaceutical and Biomedical Analysis, 2000, pp. 1143-1147.
Nakanishi, T, Enzymic studies on cheese ripening. III. Rapid fingerprinting on a mixed thin layer for qualitative analysis of casein hydrolysate, Japanese Journal of Dairy Science [Rakuno Kagaku no Kenkyu], XP-002719439, 1971, Lab. of Chem. & Tech. of Animal Products, Fae. of Agric., Tohoku Univ., Sendai, Japan, vol. 20, pp. A163-A167.
International Search Report and Written Opinion, PCT Application No. PCT/GB2013/000504, Jan. 31, 2014, 10 pages.
Co-pending PCT Application No. PCT/GB2013/000504, Nov. 20, 2013, 36 pages.

* cited by examiner

*Primary Examiner* — Maureen Wallenhorst
(74) *Attorney, Agent, or Firm* — Jason Saunders; Arnold, Knobloch & Saunders L.L.P.

(57) ABSTRACT

A ninhydrin reagent for use in a method for analyzing nitrogen-containing compounds, in particular visualizing nitrogen-containing compounds by a color forming reaction, is provided. The ninhydrin reagent contains ninhydrin; an aqueous buffer; and a temperature-dependent reducing agent, which agent is inactive in the reduction of ninhydrin at a first temperature and active in reducing ninhydrin to hydrindantin at a second temperature, wherein the second temperature is higher than the first temperature. The reagent is particularly useful in the analysis of amino acids.

19 Claims, No Drawings

REAGENT AND METHOD USING THE SAME

The present invention relates to a novel reagent for analysing nitrogen-containing compounds, for example amino acids and the like, and to a method for using the same.

Amino acids are the components from which proteins are formed, which in turn play a key role in many biological processes. In some cases the presence or absence of a particular amino acid in an individual can seriously affect their health. For example, an individual suffering from the genetic metabolic disorder phenylketonurea cannot metabolise phenylalanine; the accumulation of which severely affects their brain development. Accordingly, methods for detecting free amino acids or determining the amino acid compositions of proteins are vital for the proper diagnosis and management of diseases. Similarly, such methods are important for the analysis of commercial drugs, food and foodstuffs, as well as protein and enzyme research and development. More generally, the detection and identification of nitrogen-containing compounds finds applications across a wide range of disciplines, including, agricultural, biochemical, clinical, environmental, food, forensic, histochemical, microbiological, medical, nutritional, plant and protein sciences.

At present, free or hydrolytically released amino acids are typically detected using automatic amino acid analysers. In the 1950's the first automated amino acid analysis method was developed by Moore, Stein and Spackman, (Spackman D H, Stein W H, and Moore S. *Automatic recording apparatus for use in the chromatography of amino acids. Anal Chem,* 1958, 30:1190-1206). This multi-stage process involves separating the amino acids by ion exchange liquid chromatography. A ninhydrin reagent is pumped from a reagent reservoir, mixed with the eluent from the ion exchange column and passed through a steel or plastic reaction coil, heated to the temperature required for reaction. Ninhydrin reacts with all amino acids and related amine compounds to form highly coloured reaction products. Ruhemann's purple is formed by primary amines and primary amino acids and may be measured by absorbance of light at a wavelength of 570 nm. Other coloured reaction products, in particular yellow reaction products, are formed by secondary amines and a number of secondary amino acids. These reaction products may be measured by its absorbance of light at a wavelength of 440 nm. The coloured reaction products vary in intensity according to the concentration of amino acid.

The amino acid reaction products are passed through a photometer where the light absorbed by the dye complexes is detected at suitable wavelengths, in particular 570 nm and 440 nm. The presence of different amino acids may be determined by chromatography. The identity of each amino acid is established on the basis of its migration characteristics and thus its position on the chromatogram. The concentration of the amino acid is determined by the intensity of the coloured product detected in the photometer by way of absorbance at the specified wavelength. Accordingly, this method may be used qualitatively and quantitatively to determine which amino acids are present in a test sample and the relative concentrations of each.

The colour reaction between ninhydrin and the amino acid or amine is very slow at room temperature. It is significantly faster at elevated temperatures, but still takes many minutes, even at a temperature of 130° C. and above. To maintain good chromatographic performance the colour reaction needs to take place in a time period of around one minute or less. To achieve this, hydrindantin, the reduced form of ninhydrin, was found to be required for the ninhydrin reagent to be effective and provide an acceptable rate of reaction. There have been a number of suggested reasons or mechanisms for explaining the ability of hydrindantin to speed up the formation of the coloured products at elevated temperatures. One suggestion is that hydrindantin acts as a stabiliser for one of the reaction intermediates. As such it is considered as an accelerator not a catalyst.

The term 'ninhydrin reagent' refers to a solution or solutions containing all of the constituents necessary for use in the amino acid analysers. Accordingly, a ninhydrin reagent comprises hydrindantin, ninhydrin and the requisite buffers and solvents. The ninhydrin reagent may be formed by adding a separate solution of hydrindantin to the ninhydrin solution. Although, it would be preferable provide one solution comprising all of the constituents necessary for amino acid analysis, an unacceptably low shelf life of the ninhydrin reagent would result. Alternatively, hydrindantin may be produced in situ by adding a reducing agent to the ninhydrin solution, thereby reducing a portion of the ninhydrin to hydrindantin. The formation of hydrindantin in situ occurs more or less instantaneously in the presence of a strong reducing agent. However, both of these methods require the user to mix a separate solution of ninhydrin with a separate solution of hydrindantin or a suitable reducing agent before the ninhydrin reagent is ready to be used in the amino acid analysis.

In recent times it has become the preferred practice for manufacturers to provide two bottles, one comprising a solution of hydrindantin in an organic solvent and the other comprising a solution of ninhydrin, an aqueous buffer and an additional organic solvent, both bottles being tightly sealed under an inert gas atmosphere. The contents of the bottles are then mixed to form the ninhydrin reagent shortly before or immediately prior to use in an amino acid analyser.

Unfortunately, hydrindantin is a very difficult reagent to handle. It is particularly unstable in the presence of air, the oxygen rapidly oxidising the hydrindantin back to ninhydrin. Only relatively small amounts of air are necessary to seriously deplete the hydrindantin and thus substantially reduce the sensitivity of the colour production. If air is not rigidly excluded from the reagent, the hydrindantin concentration will slowly drop until no colour reaction will take place in the time frame of the chromatographic analysis.

Exposure of a ninhydrin reagent comprising hydrindantin to the surrounding air must therefore be kept to an absolute minimum as even minute traces of oxygen exposure will cause a steady loss in hydrindantin activity. An inert atmosphere, usually nitrogen, may be used both in the preparation and during use of the ninhydrin reagent. As can be appreciated, this requirement results in the need for complex equipment and handling procedures, to ensure hydrindantin activity does not deteriorate at an unacceptable rate before and/or during its use. Notwithstanding these precautions being used, a ninhydrin reagent comprising hydrindantin will typically have a shelf life of no longer than one month.

In addition, hydrindantin is insoluble in totally aqueous media. However, hydrindantin is soluble in a number of organic solvents. Accordingly, organic solvents are generally added in relatively high proportions to the reagent to reduce the possibility of precipitation of hydrindantin during storage and use. Indeed, organic solvent contents up to as high as 75% by volume are typically used. The solvent may also comprise a combination of two or more different types of solvent, to ensure adequate dissolution of hydrindantin. Organic solvents used for this purpose typically include dimethylsulfoxide (DMSO), methylcellosolve, ethylene glycol and sulfolane. Yet still, if insufficient organic solvent is used or the hydrindantin concentration is too high, precipitation may occur on standing or build up in the chromatographic apparatus, blocking the tubing.

In light of the above mentioned difficulties associated with using hyrdrindantin, alternative techniques and equipment for amino acid analysis using typical ninhydrin reagents have been proposed. For example, U.S. Pat. No. 3,632,496 discloses a reagent generator formed from an elongated housing having a channel through including an inlet at one end for receiving a reagent and an outlet at the other for discharging activated reagent. The channel is defined by surfaces of metallic material catalytically active for reducing ninhydrin to form the activated reagent. In this way, ninhydrin in its stable state may be stored and activated in one vesicle.

U.S. Pat. No. 4,359,323 relates to a liquid chromatograph analytical system for amines. The system consists of a chromatographic column, a reaction column and a loop to recycle the mobile phase for reuse. The primary and most significant feature of this system is that the liquid mobile phase is comprised of a combination of an eluent and a substance which reacts with amines to produce a compound which can be detected photometrically. Accordingly, this process only requires a single pump for complete operation. In spite of the reduced complexity of the pumping system, the presence of hydrindantin in the mixture will still give the same problems of instability and air sensitivity as with present commercial reagents.

In addition to the above, a number of reducing agents have been assessed for their suitability for use in reagents necessary for amino acid analysis Reducing agents for ninhydrin are preferably highly soluble in the reagent solution, have an excellent reducing property against ninhydrin, do not form coloured by products, are inert to the equipment, and are stable and easy to handle. However, as is discussed in more detail below, existing reducing agents do not exhibit all of these characteristics and therefore interfere to a significant degree with the sensitivity and accuracy of amino acid analysis in one or more ways.

During the continuing development of the ninhydrin reagent, a lot of attention has been paid to the use of strong reducing agents to produce hydrindantin in situ. The original method by Moore, Stein and Spackman employed stannous chloride as the reducing agent. However, the amount of stannous chloride required to produce sufficient hydrindantin for a reasonably fast reaction caused eventual precipitation of tin hydroxide compounds, which in turn fouled and blocked the flow tubing. The use of stannous chloride was therefore soon abandoned and other reducing agents such as cyanide, titanous salts, borohydride and ascorbic acid were investigated. Cyanide could not be used commercially because of toxicity issues and lacked the necessary stability. More serious studies were carried out on sodium borohydride and ascorbic acid reducing agents.

For example, U.S. Pat. No. 3,778,230 discloses a colour developing solution for use in automatic amino acid analysis by Liquid Chromatography, wherein ascorbic acid is used as the reducing agent. In the method described, ascorbic acid is reacted with ninhydrin in the presence of methyl cellosolve to form hydrindantin. Ascorbic acid was found to have several advantages, such as increased solubility, a potent reducing property and sensitivity of colouration. In addition, ascorbic acid is readily regenerated after deterioration compared with conventional reducing agents, such as stannous chloride.

Despite these advantages, the ninhydrin reagent disclosed in U.S. Pat. No. 3,778,230 comprising ascorbic acid as reducing agent is vulnerable to oxidation. The ninhydrin reagent must first be prepared, typically in an inert container, at ambient temperatures. As a consequence, elaborate and time consuming procedures are necessary in order to minimise the risk of oxidation of hydrindantin. In addition, a considerable amount of time elapses in the method whilst separated amino acids are introduced to the ninhydrin reagent before reaching the heated reaction coil, thus distorting the results recorded in the chromatogram. In addition, during this time, the ninhydrin reagent may be exposed to oxygen which has diffused into the analysis equipment. In fact U.S. Pat. No. 3,778,230 admits that the deterioration characteristics of the ninhydrin reagent comprising ascorbic acid were only equivalent to that of Moore, Stein and Spackman comprising stannous chloride (i.e. 15 days). Recovery of the colouring capacity after deterioration due to air oxidation necessitates re-addition of ascorbic acid. An analogous approach would not have been possible using the conventional Moore, Stein and Spackman method, due to the low solubility of stannous chloride.

Perhaps one of the most notable disadvantages to using ascorbic acid as a reducing agent is that it is known to form brown coloured decomposition matter upon heating alone. U.S. Pat. No. 3,778,230 suggests that the reduction products of reacting ascorbic acid with ninhydrin are not brown coloured. However, there is a high risk that use of ascorbic acid as reducing agent results in the formation of coloured by-products as a result of thermal decomposition of the ascorbic acid, thereby adversely affecting the accuracy of the results recorded by the chromatogram.

In a further example, U.S. Pat. No. 4,274,833 discloses a ninhydrin reagent comprising a reducing agent (sodium borohydride or stannous chloride) or hydrindantin itself, as well as a sulfolane water miscible organic solvent. Employing sulfolane as the solubilising agent is suggested to have many advantages. In particular, sulfolane solubilises hydrindantin and ninhydrin very well and does not react with any of the solution components. Accordingly, the reagent is stable for long periods of time without precipitation, known to result in the clogging of flow lines. The lifetime of the ninhydrin reagent comprising hydrindantin, is claimed to be at least 3 months. However, as is the case with U.S. Pat. No. 3,778,230, the ninhydrin reagent must first be prepared, typically in an inert container, at ambient temperatures. As discussed above, this requires elaborate and time consuming procedures in order to minimise the risk of oxidation of hydrindantin.

Little has changed in the last 60 years since the discovery of ninhydrin based analysis requiring hydrindantin by Moore, Stein and Spackman. Rather, this method is still the most common technique used today. Although this method has since been modified by using different reducing agents and/or solvents, disadvantages still include vulnerability to oxidation and low solubility in aqueous solutions as highlighted above.

Despite considerable research having been conducted with regard to finding alternative reducing agents, manufacturers have generally reverted to providing separate solutions of hydrindantin and ninhydrin. Typically, manufacturers provide two bottles, the first comprising a solution of hydrindantin in an organic solvent and the second comprising a solution of ninhydrin, an aqueous buffer and additional organic solvent; both bottles being tightly sealed under an inert gas atmosphere. The bottles are then mixed to form the ninhydrin reagent prior to use in an amino acid analyser.

Most manufacturers claim a maximum shelf life of about 12 months before mixing and 2 to 3 months after mixing. However, the life time of the mixed reagent is even lower once attached to the analysis instrument and can be significantly below 1 month.

Hitachi appears to be the only major manufacturer to provide a reducing agent for producing hydrindantin, in particular sodium borohydride. Sodium borohydride is not easy to handle, nor is it particularly stable reducing agent. Reasonable stability is only achieved if kept in non-aqueous solvents. The main advantage to using sodium borohydride as reducing agent is that no unwanted coloured products or precipitates are produced. Two bottles during manufacture are still required however, but the composition and means of mixing is rather different from the methods described above. One bottle contains sodium borohydride, ninhydrin and a non-aqueous solvent. The other bottle contains an aqueous buffer and additional non-aqueous solvent. It can be assumed that the borohydride does not react with the ninhydrin until mixed with the aqueous reagent.

Unlike the Moore, Stein and Spackman method, sodium borohydride and ninhydrin are mixed together in-line before the heated reaction chamber of the analyser. Accordingly, it has been asserted that the Hitachi reagent may be used for up to a maximum of 12 months from opening a sealed container of the reagent, rather than the standard 1 month. Nevertheless, borohydride is still not fully stable and it is known that the presence of trace metals will accelerate its deterioration. As a result, a significant amount of the borohydride will typically be lost before the end of one year. Although, in use, hydrindantin is produced in-line, an extra pumping system or line is necessary for introducing sodium borohydride into the analysis equipment. This increases the complexity and cost of the system and the Hitachi reagent may not be usable on all instruments, unless they are fitted with such an additional pumping system and supply lines. Further, in use, hydrindantin is formed from ninhydrin before contacting the eluted amino acids in the heated reaction chamber.

It is clear that there remains a need for an improved ninhydrin reagent, which is less vulnerable to oxidation and thus more easily handled before and during use and provides a longer shelf life.

Accordingly, in a first aspect, the present invention provides a ninhydrin reagent for use in a method for visualising nitrogen-containing compounds, the ninhydrin reagent comprising:
    ninhydrin;
    an aqueous buffer; and
    a temperature-dependent reducing agent, which agent is inactive in the reduction of ninhydrin at a first temperature and active in reducing ninhydrin to hydrindantin at a second temperature, wherein the second temperature is higher than the first temperature.

As noted above, the present invention provides a ninhydrin reagent for visualising nitrogen containing compounds, including but not limited to amino acids. The ninhydrin reagent comprises a temperature-dependent reducing agent having a specific set of properties, as discussed in more detail below. As a result of this, unlike known and/or commercially available ninhydrin reagents, the components of the ninhydrin reagent of the present invention do not need to be stored separately and premixed just before use, and hence may be stored and provided to a user in one bottle. In light of this, use of the ninhydrin reagent of the present invention will be less complex and less expensive than those which are currently commercially available.

The ninhydrin reagent of the present invention does not need to comprise hydrindantin and is preferably substantially free from hydrindantin. This is an advantageous aspect of the reagent of the present invention.

The components of the reagent are stable at the first, lower temperature, at which they may be transported and stored. Hydrindantin is formed when the components of the ninhydrin reagent are heated to the second temperature, at which temperature the reducing agent is active in the reduction of ninhydrin to hydrindantin. Accordingly, the ninhydrin reagent is easily handled and controlled both before and during use on the amino acid analysis equipment. In fact, the ninhydrin reagent of the present invention may be stored and used very easily and efficiently in the presence of air for a considerable period of time. It is has been found that the ninhydrin reagent of the present invention may have a shelf life well in excess of 2 years.

In light of the above, the ninhydrin reagent of the present invention may be used for applications other than amino acid analysis using an amino acid analyser instrument. Due to its increased stability, the ninhydrin reagent may be used as a visualising agent in general, provided that the test sample comprises one or more organic nitrogen containing compounds. Whilst commercially available ninhydrin reagents may be used for purposes other than the detection of amino acids on amino acid analysers using ion exchange separation methods, an improved ninhydrin reagent having the above mentioned characteristics may be more readily applied in a wide range of other analytical methods for detecting nitrogen-containing organic compounds.

The use of the reagent of the present invention is based on the well established amino acid and ninhydrin reaction. Accordingly, the coloured reaction products may be subjected to photometry in known manner. In particular, the relative absorbance sensitivities obtained at the two most popular wavelengths of 570 nm and 440 nm, are similar when using the present invention as presently achieved in amino acid analysers using commercially available reagents. For many applications, only one monitoring wavelength may be required to determine primary and secondary amino acids.

As noted above, the reagent of the present invention comprises a temperature-dependent reducing agent. A range of temperature-dependent reducing agents inactive in the reduction of ninhydrin at a first temperature have been found to be capable of reducing ninhydrin to form hydrindantin at a second temperature, higher than the first temperature.

Unlike with commercially available ninhydrin reagents therefore, the temperature-dependent reducing agents of the present invention are highly stable in the presence of oxygen at the first temperature. Accordingly, elaborate and time consuming procedures are not required to circumvent deterioration of the reagents prior to use. Further, the formation and the rate of formation of hydrindantin from ninhydrin can be controlled by varying the temperature. In this way, hydrindantin is produced only when required, increasing the lifetime of the ninhydrin reagent during use and reducing cost.

A compound is suitable for use as the temperature-dependent reducing agent of the ninhydrin reagent of the present invention, provided it is inactive in the reduction of ninhydrin at the first temperature and active in reducing ninhydrin to hydrindantin at the second temperature, wherein the second temperature is higher than the first temperature. In this respect, the term 'inactive' when used in relation to the reduction of ninhydrin at the first temperature is a reference to the compound having an activity at or below a maximum activity. Similarly, the term 'active' when used in relation to the reduction of ninhydrin at the second temperature is a reference to the compound having or exceeding a minimum activity, as discussed in more detail below.

Compounds for use in forming the temperature-dependent reducing agent of the ninhydrin reagent may have a reducing activity capable of reducing ninhydrin at a rate comparable to those of known reducing agents. However, it is preferred that the temperature-dependent reducing agent of the ninhydrin reagent is less active and reduces ninhydrin at a lower rate than those reducing agents employed commercially. This has the advantage of easier control of the reduction reaction.

In order to assess whether a particular compound has sufficient activity in the reduction of ninhydrin at the second temperature, a first Protocol has been devised; details of which are provided in Example 1. Compounds meeting the requirements of Protocol 1 are considered to have at least a minimum activity in the reduction of ninhydrin to hydrindantin at an elevated or second temperature.

According to the method of Protocol 1, a compound is considered sufficiently active in reducing ninhydrin if at a threshold temperature, that is the second temperature, it has a minimum degree of activity, that is, is able to reduce a given amount of ninhydrin in a specified period of time. In this protocol, the threshold temperature is 100° C.

According to the test protocol, ninhydrin and an amino acid solution is mixed with a solution of the selected compound at a threshold temperature of 100° C. After 20 minutes, the intensity of Ruhemann's purple produced, if any, is calculated by measuring the absorption of the solution using a standard spectrophotometer at a specified wavelength of 570 nm. A strong intensity of colouration indicates that the selected compound has a high degree of activity at the threshold temperature. More preferably, for the purposes of assessing whether the selected compound has the minimum degree of activity required for forming part of the ninhydrin reagent of the present invention, a minimum absorbance of 0.3 is required. The minimum activity of the compound in the reduction of ninhydrin at the second temperature is one that provides an absorbance of at least 0.3 in the aforementioned test. An absorbance below about 0.3 indicates that the compound is not sufficiently active at elevated temperatures in the reduction of ninhydrin for use in the ninhydrin reagent of the present invention. More preferably, the minimum absorbance to be achieved by the candidate compound is at least 0.4.

In addition to the above, compounds for use in forming the temperature-dependent reducing agent in the ninhydrin reagent of the present invention must be inactive in the reduction of ninhydrin at a first temperature.

The first temperature at which the compounds are required to be inactive is lower than the second temperature. Typically, the first temperature is a temperature or range of temperatures at which the reagent is typically stored and/or transported, prior to use in an amino acid analyser or for the purposes of visualising nitrogen containing compounds in general. Existing ninhydrin reagents are typically stored at room temperature or below. Accordingly, the first temperature is preferably room temperature. As room temperature typically varies due to external factors, the first temperature is preferably up to 30° C., still more preferably up to 25° C., more preferably still at or below 20° C. The first temperature is preferably greater than 0° C., still more preferably greater than 5° C., more preferably still greater than 10° C. In one embodiment, the first temperature is from 5° C. to 25° C. Yet still more preferably the first temperature is from 10° C. to 20° C.

The compounds identified as being inactive at the first temperature include compounds which are not normally considered to have any significant reducing action at the first temperature but which become sufficiently strong reducing agents at the second temperature, reacting with ninhydrin to form hydrindantin. In addition, the temperature-dependent reducing agents identified as being inactive at the first temperature include compounds known to have only weak reducing activity (that is below the maximum activity defined above) at the first temperature, but which become sufficiently strong reducing agents at the second temperature, reacting with ninhydrin to form hydrindantin.

In order to determine whether a compound is sufficiently inactive at the first temperature, a second Protocol has been devised; details of which are provided in Example 2. Protocol 2 may be performed prior to or after Protocol 1 provided in Example 1. More preferably, Protocol 2 is performed after Protocol 1 has been used to establish that the selected compound has the minimum degree of activity required at the threshold or second temperature for the reduction of ninhydrin.

According to the method of Protocol 2, a ninhydrin reagent comprising the selected compound is prepared and stored at the first temperature in the presence of air. At set time intervals, a sample is taken from the ninhydrin reagent, mixed with an amino acid solution and heated to the second temperature. For the purposes of continuity with respect to Protocol 1 provided in Example 1, the second temperature is 100° C., as discussed above. The intensity of Ruhemann's purple produced, if any, is calculated by measuring the absorption spectra of the solution using a standard spectrophotometer. Measuring the intensity over successive samples, in particular determining the rate of any decrease in intensity of coloration, indicates whether the long term stability of the selected compound is suitable for the compound to be used in the ninhydrin reagent of the present invention.

According to Protocol 2, a selected compound is deemed not to be sufficiently stable at the first temperature and therefore not suitable for use in the ninhydrin reagent of the present invention, if the corrected absorbance drops to less than 50% after 1 month. That is, compounds suitable for use in forming the temperature-dependent reducing agent in the ninhydrin reagent of the present invention have an activity of at least 50% of their initial activity after 1 month. More preferably, the selected compound is considered suitable for use in the ninhydrin reagent of the present invention, if the corrected absorbance is no less than 50% after 3 months, still more preferably if the corrected absorbance is no less than 50% after 6 months. Particularly preferred compounds are those in which the corrected absorbance in Protocol 2 is at least 50% after 12 months, still more preferably if the corrected absorbance is at least 50% of the initial absorbance after 24 months.

It has been found that compounds having the properties set out above and able to meet the requirements of Protocol 1 of Example 1 and meet or exceed the requirements of Protocol 2 of Example 2 are most advantageous for use in a ninhydrin reagent. As noted above, using the methods provided in both Examples 1 and 2, a range of compounds have been found to be sufficiently stable at the first temperature whilst also having the minimum degree of activity required at the second temperature for use in the ninhydrin reagent of the present invention. While these compounds may vary according to their degree of activity at the second temperature, they all have the minimum degree of activity required for use in the ninhydrin reagent of the present invention.

As indicated, Protocol 1 of Example 1 and Protocol 2 of Example 2 have been used to screen a range of compounds for their suitability for use as the temperature-dependent reducing agent of the ninhydrin reagent of the present invention. The ninhydrin reagent may comprise a single temperature-dependent reducing agent. Alternatively, the reagent may comprise a combination of two or more temperature-dependent reducing agents.

Suitable compounds for use as the temperature-dependent reducing agent of the ninhydrin reagent of the present invention are known in the art and are commercially available In one embodiment, the temperature-dependent reducing agent comprises one or more saccharides. The saccharides may be conveniently grouped into monosaccharides, disaccharides and polysaccharides.

Many saccharides have mild reducing properties and are sometimes called reducing sugars. A reducing sugar can be defined as one containing a hemiacetal or hemiketal group in its cyclic form producing an aldehyde or ketone group in its open ring form. All monosaccharides and many disaccharides are reducing sugars.

Preferred monosaccharides include glucose and fructose, which in their cyclic forms have a hemiacetal and a hemiketal group respectively. Glucose and fructose were both found to have sufficient reducing activity at the second, threshold temperature whilst remaining stable at the first temperature in the presence of air, when subjected to the aforementioned Protocol 1 and Protocol 2.

Fructose was found to have a shelf life of approximately 3 years at room temperature. Although not as reactive in the reduction of ninhydrin at the second temperature, glucose was found to be more stable than fructose, having a shelf life of longer than 4 years at room temperature. Accordingly, if a longer shelf life is required, the ninhydrin reagent of the present invention preferably comprises glucose.

Other monosaccharides for use as the temperature-dependent reducing agent of the ninhydrin reagent of the present invention include such compounds as glyceraldehyde and galactose, which are both aldoses. A non exhaustive list of monosaccharides which have been found to be capable of forming the temperature-dependent reducing agent of the present invention includes the aldoses, Ribose, Xylose, Erythrose, Threose, Lyxose, Arabinose, Allose, Altrose, Mannose, Gulose, Idose, Talose and L-Glycero-D-manno-heptose and the ketoses Dihydroxyacetone, Erythrulose, Ribulose, Xylulose, Psicose, Sorbose, Tagatose and Sedoheptalose. An aldose is a monosaccharide which has an aldehyde group in its linear form and a ketose is one which has a ketone group in its linear form.

In general, some disaccharides and polysaccharides will not have the properties required to form suitable temperature-dependent reducing agents as defined by the test Protocol and batch stability test. For the disaccharides they can be reducing or non-reducing sugars. For example sucrose is a non-reducing disaccharide and it was found to be not sufficiently active in the reduction of ninhydrin to hydrindantin when assessed according to Protocol 1 and 2. However, there are a significant number of disaccharides and polysaccharides comprising a hemiacetal or hemiketal group in their cyclic form. These types of saccharides are capable of acting as temperature-dependent reducing agents as defined by Protocol 1 and 2. The disaccharides, lactose and maltose are two such examples.

A non exhaustive list of disaccharides which have been found to be capable of forming the temperature-dependent reducing agent of the present invention includes Trihalose, Cellobiose, Kojibiose, Nigerose, Isomaltose, Sophorose, Laminaribiose, Gentiobiose, Turanose, Maltulose, Palatinose, Gentiobiulose, Mannobiose, Melibiose, Melibiulose, Rutinose and Xylobiose.

Longer chain polysaccharides can be effective temperature-dependent reducing agents; the tetrasaccharose, stachyose, is one such example. Whilst much longer chain polysaccharides, such as starch are not suitable, partially hydrolysed starch such as the dextrins and maltodextrins can be effective temperature-dependent reducing agents. It is to be appreciated that whilst long chain polysaccharides may be suitable temperature-dependent reducing agents, they are not preferred as they can give more viscous solutions and increase the possibility of precipitation.

The temperature-dependent reducing agent may also comprise one or more carboxylic acids and/or their salts. In general, simple monofunctional carboxylic acids, comprising only a single carboxylic acid group and no other functional group, have not been found capable of acting as temperature-dependent reducing agents according to Protocol 1 and 2. Such monofunctional carboxylic acids include acetic, propionic, and benzoic acid. However, formic acid and its salts have been found to be capable of acting as temperature-dependent reducing agents according to Protocol 1 and 2.

Suitable salts of carboxylic acids for use in the temperature-dependent reducing agent include metal salts, in particular Group I and Group II metal salts, for example potassium, sodium, calcium and magnesium salts. Sodium formate, the sodium salt of formic acid was found to be sufficiently active in reducing ninhydrin to hydrindantin at a second temperature and sufficiently inactive in the reduction of ninhydrin at a first temperature according to Protocol 1 and Protocol 2 respectively. In particular, sodium formate was found to have a reducing activity in-between that of glucose and fructose. Further, the shelf life was similar to that of glucose having a shelf life in excess of 4 years.

Other carboxylic acids and/or their salts suitable for use as temperature-dependent reducing agents according to the present invention are those comprising at least one additional reducing group, for example one or more of a hydroxy ketone or aldehyde group. Suitable salts of the carboxylic acids include metal salts, for example salts of metals in Groups I or II of the Periodic Table. Examples of suitable salts include potassium, sodium, magnesium and calcium salts.

Preferred carboxylic acids have from 1 to 24 carbon atoms, more preferably 1 to 18 carbon atoms, still more preferably from 1 to 12 with $C_1$ to $C_6$ aldehydes and ketones being especially preferred. The compounds may be straight chained, branched or cyclic.

Further, compounds comprising one or more aldehyde and ketone groups, with or without the presence of hydroxyl groups, (including the simple aldehydes and ketones themselves) have been found to meet the requirements of Protocols 1 and 2. Preferred compounds of this type have from 1 to 24 carbon atoms, more preferably 1 to 18 carbon atoms, still more preferably from 1 to 12 with C1 to C6 aldehydes and ketones being especially preferred. The compounds may be straight chained, branched or cyclic. Examples of suitable aldehydes and ketones include acetone.

The temperature-dependent reducing agent may also comprise one or more inorganic compounds, provided they too meet the requirements of Protocol 1 and 2. In particular, inorganic compounds comprising sulphur in low oxidation states such as sulfite and thiosulfate and/or inorganic compounds comprising phosphorus oxyacids in low oxidation states such as phosphites and hypophosphites may be particularly suitable. For example, it has been found that phosphorous acid, including its phosphite salts such as lithium, sodium and potassium, passes both Protocol 1 and 2 with an activity between that of fructose and sodium formate.

The temperature-dependent reducing agents for use in the ninhydrin reagent of the present invention are generally known in the art and are either commercially available or may be prepared in a manner analogous to known synthesis routes.

It is to be appreciated that other compounds or classes of compounds which have not been identified above may be suitable components for use as the temperature-dependent reducing agent of the ninhydrin reagent of the present invention, provided they meet the requirements of both Protocol 1 of Example 1 and Protocol 2 of Example 2. In general, in addition to meeting the requirements of Protocol 1 and Protocol 2, the temperature-dependent reducing agent should be readily soluble in or miscible with water and not cause precipitation when combined with other components of the reagent and/or the components used or produced in the analysis methods. It is also advantageous that the temperature-dependent reducing agent is substantially non-toxic.

In light of the above the ninhydrin reagent may comprise the temperature-dependent reducing agent in any suitable concentration. This will vary according to the temperature-dependent reducing agent employed, in particular according to such factors as the degree of activity at the second temperature. The concentration of the temperature-dependent reducing agents may be from 0.01% to 75% w/v or v/v. More preferably, the concentration of the temperature-dependent reducing agents is from 0.01% to 20% w/v or v/v. It has been found that at concentrations higher than 20% w/v or v/v, components of the reagent may be more likely to precipitate out of solution or cause other components to precipitate out of solution and accordingly concentrations below 20% are to be preferred.

When preparing the ninhydrin reagent for use in an analytical method, the starting concentration of the temperature-dependent reducing agent is preferably similar to that which was identified in Protocol 1 provided according to Example 1, as responsible for providing an actual absorbance of at least 0.3, more preferably an absorbance from 0.3 to 0.7. More preferably, as a result of repeating the test Protocol according to Example 1 several times, each time increasing the percentage concentration of the temperature-dependent reducing agent, the concentration which provides the highest absorbance between 0.6 and 0.7 without precipitating out of solution or adversely affecting the other components of the ninhydrin reagent is used as the starting concentration.

The ninhydrin reagent of the present invention further comprises ninhydrin and an aqueous buffer. Ninhydrin and suitable aqueous buffers are both commercially available and used in existing ninhydrin reagents.

The ninhydrin reagent of the present invention may comprise ninhydrin in any suitable amount. Preferably, the concentration of ninhydrin in the reagent is from 0.5 to 3% w/v. More preferably, the concentration of ninhydrin is from 1 to 2.5% w/v. Yet still more preferably, and as Protocol 1 according to Example 1, the concentration of ninhydrin in the reagent is about 2% w/v.

Any suitable aqueous buffer may be used in the ninhydrin reagent. Suitable buffers are known in the art. An acidic buffer is preferred. More preferably, a weak acidic buffer is preferred so as to maintain the pH at a value of between 3 to 7, more preferably from 4 to 6, still more preferably from 4.5 to 5.5. A particularly suitable pH is about 5.2.

The buffer may be prepared from any weak acid and one of its conjugate bases/salts. The acid may be an organic acid or an inorganic acid. Organic acids are preferred, examples of which include acetic acid, ethanoic acid and propanoic acid. One preferred combination is acetic acid and one of its salts. The acid salt may be any suitable salt. The salt may be formed from any metal cation. However it is preferable that the salt is formed from any one of the alkali metals, in particular lithium, sodium or potassium.

As noted above, hydrindantin is insoluble in a totally aqueous media. In light of this, commercially available ninhydrin reagents, comprising hydrindantin, cannot be manufactured or used without the presence of a substantial amount of organic solvent. It is an advantage of the present invention however, that the ninhydrin reagent need not comprise an organic solvent or mixture of organic solvents. As a consequence, the manufacturing costs are reduced, the reagent is less harmful to the environment and waste disposal procedures are simplified.

The presence of an organic solvent in the ninhydrin reagent may affect the efficacy of the reagent. The sensitivity of the reagent of some embodiments of the present invention that do not comprise an organic solvent has been found to be approximately 30% lower than that of commercially available reagents which comprise an organic solvent or mixture of organic solvents. In addition, in the absence of organic solvents, there may be a greater risk of precipitation of the resulting hydrindantin.

Notwithstanding the above, the reagent of the present invention, when formulated without an organic solvent, provides at least acceptable results when used for amino acid analysis. In addition, optimisation of the concentration of the temperature-dependent reducing agent according to Protocol 1 and 2 will minimise the risk of precipitation.

In an alternative and preferred embodiment, the ninhydrin reagent of the present invention further comprises an organic solvent or mixture of organic solvents. Organic solvents typically used in commercially available reagents include, dimethylsulfoxide, ethylene glycol, propylene glycol, sulfolane, hydroxy ethers such as carbitol, propylene glycol monomethyl ether and methylcellosolve and simple alcohols such as methanol, either alone or as mixtures. The addition of an organic solvent will increase the sensitivity of the ninhydrin reagent of the present invention. This should be taken into account when using the preferred ninhydrin reagent on a chromatographic system, as is discussed in more detail below.

The total concentration of organic solvent used will vary according to the nature of the organic solvent. In particular, the total concentration of organic solvent used will vary from 10% v/v to 75% v/v. More preferably, the total concentration of organic solvent used will vary from 25% v/v to 65% v/v. Yet still more preferably, the total concentration of organic solvent used will vary from 35% v/v to 55% v/v. Whilst any of the above commercially available organic solvents may be used, in accordance with the chromatography examples shown below, the method of the present invention preferably employs 40% v/v to 55% v/v ethylene glycol.

The ninhydrin reagent of the present invention may be used in accordance with known and standard procedures and methods for the detection of nitrogen-containing compounds. The ninhydrin reagent used in such methods is that which has been defined above in the first aspect of the present invention. Accordingly, the ninhydrin reagent comprises a temperature-dependent reducing agent inactive at a first temperature and active at a second threshold temperature to reduce ninhydrin to form hydrindantin according to Protocol 1 and Protocol 2 provided in Examples 1 and 2 respectively.

As previously discussed, the ninhydrin reagent of the present invention must be inactive at a first temperature and active at a second temperature to reduce ninhydrin to form hydrindantin, wherein the second temperature is higher than the first. Due to its increased stability, the ninhydrin reagent of the present invention may be used as a visualising agent to identify and/or quantify a wide range of nitrogen-containing compounds.

In a preferred embodiment however, the ninhydrin reagent of the present invention is used for amino acid analysis, in particular using known and standard amino acid analysers.

Accordingly, in a second aspect, the present invention provides for the use of a ninhydrin reagent in a method for analysing nitrogen-containing compounds, in particular amino acids and the like, wherein the ninhydrin reagent comprises;

ninhydrin;

an aqueous buffer; and a temperature-dependent reducing agent, which agent is inactive in the reduction of ninhydrin at a first temperature and active in reducing ninhydrin to hydrindantin at a second temperature, wherein the second, threshold temperature is higher than the first temperature The ninhydrin reagent may be used in a method for analysing, for example identifying and/or quantifying, one or more nitrogen-containing compounds. The method is suitable for analysing a range of nitrogen-containing compounds. In fact, as noted above the method may be used for analysing both organic and inorganic nitrogen containing compounds.

The ninhydrin reagent may be used in a method for analysing, for example identifying and/or quantifying, one or more nitrogen-containing compounds. The method is suitable for analysing a range of nitrogen-containing compounds. In fact, as noted above the method may be used for analysing both organic and inorganic nitrogen containing compounds.

The method of the present invention is particularly suitable for analysing amino acids and compounds formed from amino acids, such as proteins, peptides, and the like. The following description describes the analysis of amino acids. It is to be understood that the other aforementioned nitrogen-containing compounds may be processed in an analogous manner.

The nitrogen-containing compounds may be present in any liquid medium or stream. The method of the present invention is particularly suitable to the analysis of an eluent from the outlet of an ion exchange column containing one or more amino acids in an ion exchange liquid chromatography procedure.

The method of the present invention may be carried out using a conventional automatic amino acid analyser. As noted above, automatic analysers typically comprise means for separating amino acids into their respective components, an input system for introducing a ninhydrin reagent into the system, allowing the separated amino acids and ninhydrin reagent to react at elevated temperatures to form coloured substances and means for recording the absorbance of the coloured substances at specified wavelengths. In this way, the amino acids present within a test sample and the relative concentrations of each may be determined.

Amino acids are typically separated using techniques which discriminate on the basis of size, solubility, charge and/or binding affinity. At present, the most common technique used to separate amino acids discriminates on the basis of net charge and is therefore known as ion exchange chromatography. The present invention provides a method which may be used effectively in association with ion exchange chromatography as well as other forms of chromatographic separation techniques, column and planar, including but not limited to gel filtration chromatography, affinity chromatography and high or low pressure liquid chromatography, involving normal phase, reverse phase and adsorption separation mechanisms. In addition, the present invention provides a method which may be used in association with non-chromatographic separation techniques such as column electrophoresis. Furthermore, the reagent may effectively be used for techniques not necessarily involving chromatographic separation such as fingerprint visualization and colour development in tubes or containers.

In one embodiment, the present invention is applied as part of an ion exchange chromatography procedure, comprising passing the amino acid-containing solution through a resin packed ion exchange column to separate the amino acid sample into the respective amino acid components by differences in their migration speeds down the column. The eluted amino acids are then free to react with a colour developing solution according to the method of the present invention.

As discussed above the colour developing solution is comprised of ninhydrin, a temperature-dependent reducing agent inactive at a first temperature and active at a second threshold temperature to reduce ninhydrin to form hydrindantin, an acetate buffer and preferably an organic solvent.

The ninhydrin reagent as described above, is suitable for use on a standard amino acid analyser. As discussed above, existing amino acid analysers comprise a single heated reaction chamber. This is also known as the colour forming chamber, as this is where Ruhemann's purple is produced after the separation column effluent is mixed with the ninhydrin reagent.

The temperatures of the colour forming chamber and/or concentration of the temperature-dependent reducing agent are preferably selected in order to avoid precipitation of the resulting hydrindantin. The temperature within the colour forming chamber may be varied according to the temperature-dependent reducing agent employed and the extent to which it is capable of reducing ninhydrin at higher temperatures. In general however, the temperature of the colour forming chamber is preferably in the range of from 50° C. to 150° C., more preferably from 80° C. to 150° C. Still more preferably, the temperature of the colour forming chamber is from 120° C. to 140° C. Yet still more preferably, the temperature of the colour forming chamber is from 125° C. to 135° C.

The ninhydrin reagent and eluted amino acids are heated within the heated reaction chamber and allowed to react for a sufficient period of time, for example from 15 seconds to 5 minutes. More preferably, the ninhydrin reagent and eluted amino acids are allowed to react in the heated reaction chamber for a period of from 30 seconds to 2 minutes, more preferably about 1 minute. It is an advantage of the ninhydrin reagent of the present invention that the time required in the reaction chamber to produce the required colouration is short.

As discussed above, the components of the ninhydrin reagent of this invention react only when subjected to heating, to produce hydrindantin, which may be contacted with the amino acids to produce the coloured product for photometric analysis. In the method of the present invention, the components of the ninhydrin reagent are heated within the heated colour forming reaction chamber, typically a coil. Hydrindantin is formed in very low concentrations at the very beginning of the colour forming reaction coil and the hydrindantin concentration increases with time as the reagent continues to be exposed to the elevated temperature. In this way, the ninhydrin reagent of the present invention may be used on commercially available analysers, with no need for modifying their component parts or method of operation.

The components of the ninhydrin reagent may be introduced into the colour forming reaction chamber in a number of different ways as described herein below.

In a first embodiment, ninhydrin, a temperature-dependent reducing agent as described above, and the buffer and optionally one or more organic solvents are pre-mixed to form a homogeneous solution. This homogeneous solution is the ninhydrin reagent of the first aspect of the present invention. This is the preferred embodiment as the mixture may be formed well in advance of its use in the method of the present invention.

More preferably the mixture is drawn from one or more containers or reservoirs by one or more pumps and delivered to a common zone at any convenient point during the amino acid analysis procedure. The zone is situated downstream of the ion exchange column but upstream of the colour forming reaction chamber. This arrangement is one preferred embodiment, as commercially available analysers typically deliver ninhydrin reagents comprising hydrindantin in this way. Accordingly, the ninhydrin reagent of the present invention may be used on standard amino acid analysers with no need for modifying their component parts or their method of operation.

Yet still more preferably, the zone is situated within the colour forming reaction chamber. In this way, hydrindantin is formed immediately upon heating within the colour forming reaction chamber.

In an alternative embodiment, the components of the ninhydrin reagent are kept separate until shortly before heating and contacting with the amino acids. For example, ninhydrin and the temperature-dependent reducing agent may be drawn from a single or separate containers or reservoirs by two or more pumps and delivered to a common line or mixing zone, where they are combined to form a mixture. In this embodiment, the buffer and optional one or more organic solvents may each be drawn from a single or separate containers or reservoirs to combine with the mixture of ninhydrin and the compound inactive at room temperature.

Similarly, the common line or mixing zone is typically situated downstream of the ion exchange column but upstream of the colour forming reaction chamber. This arrangement is preferred as commercially available analysers typically deliver ninhydrin reagents comprising hydrindantin in this way. Accordingly, the ninhydrin reagent of the present invention may be used on standard amino acid analysers with no need for modifying their component parts or their method of operation.

Yet still more preferably, the zone is situated within the colour forming reaction chamber. In this way, hydrindantin is formed immediately upon heating within the colour forming reaction chamber.

The amino acid stream may be contacted with the components or mixture of components at any convenient point in the procedure. For example, the amino acids may be combined with one of the ninhydrin or temperature-dependent reducing agent, prior to forming the mixture and heating. As an alternative, the amino acids may be combined with the mixture of ninhydrin and the temperature-dependent reducing agent prior to heating. As a further alternative, the amino acids may be combined with the components of the reagent after mixing and heating has occurred and hydrindantin formed.

As noted above, a range of temperature-dependent reducing agents have been identified using Protocol 1 and 2, as being inactive at a first temperature and active at a second threshold temperature to reduce ninhydrin to hydrindantin. Protocol 1, Protocol 2 and embodiments of the present invention will now be described in the following examples.

EXAMPLES

Example 1

Protocol 1

Protocol 1 of the present invention is comprised of the following steps;
1) Prepare the following solutions:
   i) A 1M lithium, sodium or potassium acetate/acetic acid aqueous buffer at pH 5.2, containing 2% ninhydrin w/v and a chosen starting concentration (w/v or v/v) of compound X. It is preferred to start with 0.01% w/v or v/v and gradually increase the concentration in stages. High concentrations of water soluble solids or liquids, particularly approaching 50% and above may be difficult to evaluate, due to solubility problems or other adverse effects after preparation or when used on an analytical system.
   ii) A standard solution of glycine at a concentration of 1.0 mM in pure water. As previously discussed, glycine is chosen as the standard reference amino acid.
2) In a glass test tube measuring close to 15 cm long and 1.5 cm in outside diameter, add 2.0 ml of solution of i) above, 0.20 ml of the standard glycine solution ii) and 2.8 ml of pure water.
3) Place the test tube into a liquid heating bath at 100° C. and leave undisturbed for 20 minutes. Take out the test tube and cool quickly to room temperature.
4) Transfer the cooled solution into a 1 cm cuvette and measure the absorbance at 570 nm against pure water using a standard spectrophotometer or colorimeter.
5) At the same time as the compound is being assessed for activity, a blank sample should also be performed in case there are amino acid or amine impurities in the reagents. The procedure is the same as in 2) above except that the glycine standard is omitted and the quantity of pure water is increased to 3.0 ml. The absorbance is then measured at 570 nm as per 4) above.
6) The actual absorbance produced by the compound under assessment, hereafter called the corrected absorbance, is obtained by subtracting the absorbance of the blank sample from the glycine standard absorbance.

As the degree of activity of compound X is unknown, the method of the above Protocol is preferably repeated a number of times, each time gradually increasing the concentration of compound X. The concentration of compound X is to be increased until the corrected absorbance falls between 0.6 and 0.7. The maximum corrected absorbance possible when using glycine as a control is between 0.75 and 0.80, so no advantage will necessarily be gained in this Protocol assessment by increasing the concentration of the compound any further if a corrected absorbance of 0.6 to 0.7 is achieved.

If the corrected absorbance never exceeds 0.30, this indicates that compound X does not have the degree of activity required for use in the ninhydrin reagent of the present invention.

If the corrected absorbance falls below 0.30 but increasing the concentration of compound X causes it to precipitate out of solution, or causes some other adverse effect, this indicates that compound X does not have the properties required for use in the ninhydrin reagent of the present invention.

Example 2

Protocol 2

Provided, compound X is sufficiently active at elevated temperatures to meet the requirements of Protocol 1 set out in Example 1 above, the following test may be used to assess the long term stability of a ninhydrin reagent comprising compound X at room temperature and in the presence of air.

A ninhydrin reagent is prepared in a similar way to Protocol 1 of Example 1 and stored at room temperature in the presence of air. At set time intervals, a sample is taken from the ninhydrin reagent, mixed with an amino acid solution and heated to 100° C. for a set time. The amount of Ruhemann's purple produced, if any, is measured in terms of an absorbance value. The rate of decrease in intensity of coloration (absorbance) in successive samples indicates whether the long term stability of compound X is adequate for forming part of the ninhydrin reagent of the present invention.

As per Protocol 1, glycine is used as the standard amino acid as the relative sensitivities of other amino acids and amine compounds will be similar whatever reagent is used. Protocol 2 of the present invention is comprised of the following steps;

1) On day One prepare the following solutions:
i) A standard 1.0 mM solution of glycine in water.
ii) A ninhydrin reagent comprising a 1M lithium, sodium or potassium acetate/acetic acid aqueous buffer at pH 5.2, containing 2% ninhydrin w/v and a chosen concentration (w/v or v/v) of compound X. The concentration of compound X is preferably similar to that identified in Protocol 1 as the concentration at which a corrected absorbance of between 0.4 and 0.7 is achieved. 250 ml of reagent should be enough volume to last the full length of the stability trial.
2) On day one, to a standard test tube, add in succession, 2.0 ml of the ninhydrin reagent (ii), 0.20 ml of the glycine standard (i) and 2.8 ml of pure water. Mix and place the test tube in a liquid heating bath at 100° C. and leave undisturbed for 35 minutes. Take out the test tube and cool quickly to room temperature. Measure the absorbance of the test tube solution in a spectrophotometer at 570 nm against pure water using a flow cell with 1 cm path length.
3) On day one, prepare a blank test tube sample comprising 2.0 ml of reagent (ii) and 3.0 ml of pure water. This will take into account any amino acid or amine type impurities that could be present in the components used to make up the reagents. Mix and place the blank test tube in a heating bath at 100° C. and leave undisturbed for 20 minutes. Take out the test tube and cool quickly to room temperature. Measure the absorbance of the test tube solution in a spectrophotometer at 570 nm against pure water using a flow cell with 1 cm path length.
4) On day one calculate the corrected absorbance produced by compound X. This is obtained by subtracting the absorbance of the blank sample from the glycine sample absorbance, as described in Protocol 1 of Example 1
5) On day one, after steps 1 to 4 have been completed, store the reagent in a stoppered bottle at 20° C. in the dark and exposed to the air. This is achieved by leaving a large air gap approximately the same volume as the reagent in the bottle.
6) Every two to four weeks, take a sample of the reagent and repeat steps 2 and 3. Each time, calculate the corrected absorbance at 570 nm as per step 4 and compare it with that taken at day one.

Example 3

Chromatography Examples

The relative sensitivities of a number of ninhydrin reagents comprising different temperature-dependent reducing agents has been assessed using a standard amino acid analyser. As per the test Protocol and batch stability test, glycine was used as the reference amino acid.

As discussed above, the ninhydrin reagent of the present invention may optionally comprise an organic solvent or mixture of organic solvents. Accordingly, for the sake of comparison, the relative sensitivities of these ninhydrin reagents have been assessed both in the presence and in the absence of an organic solvent. As noted above, if an organic solvent is used, the total concentration will preferably vary from 35% to 55% according to the nature of the organic solvent used. In these experiments, the temperature-dependent reducing agents were all assessed in the presence of 40% Ethylene Glycol.

Chromatography experiments were conducted several times in relation to each of the temperature-dependent reducing agents, until their sensitivity was optimised. This was achieved by varying the concentration of the temperature-dependent reducing agents and/or the reaction temperature.

The starting concentration was that which was found to satisfy the conditions of the test Protocol as described above. As noted above, the starting temperature within the colour forming chamber may be varied according to the temperature-dependent reducing agent employed but is preferably in the region of from 125° C. to 135° C.

For the chromatography examples shown here, the relative sensitivities for the different reagent compositions are compared in terms of peaks heights for glycine in units of mAU. Thus, the chromatographic conditions of retention time and peak widths (that is the peak width at half height) are constant for all the analyses (See chromatographic conditions below).

The following instrument conditions were used:

Chromatographic mode—Isocratic

Column flow rate—0.45 ml/min

Ninhydrin reagent flow rate—0.30 ml/min

Temperature of heated reaction chamber—Variable between 125 and 135° C.

Reaction time—60 seconds

Injection volume—20 µl

Amount of glycine injected—2 nmoles

Retention time—5.0 minutes

Peak width at half height—0.26 minutes

Sensitivity scale—mAU (1 mAU is equivalent to 0.001 absorbance)

Example 3.1

Fructose

The sensitivity of a ninhydrin reagent comprising 0.20% w/v fructose as the temperature-dependent reducing agent was assessed using a standard amino acid analyser under the conditions specified above.

In the presence of 40% ethylene glycol, the peak height was identified as 112 mAU at a reaction temperature of 131° C.

In the absence of ethylene glycol, the ninhydrin reagent comprising 0.20% w/v fructose provided a peak height of 88 mAU at a reaction temperature of 132° C.

Example 3.2

Sodium Formate

The sensitivity of a ninhydrin reagent comprising 1% sodium formate w/v as the temperature-dependent reducing agent was assessed using a standard amino acid analyser under the conditions specified above.

In the presence of 40% ethylene glycol, the ninhydrin reagent comprising 1% sodium formate provided a peak height of 126 mAU at a reaction temperature of 133° C.

In the absence of ethylene glycol, the ninhydrin reagent comprising 1% sodium formate provided a peak height of 107 mAU at a reaction temperature of 133° C.

Example 3.3

Glucose

The sensitivity of a ninhydrin reagent comprising 2% glucose w/v as the temperature-dependent reducing agent was assessed using a standard amino acid analyser under the conditions specified above.

In the presence of 40% ethylene glycol the ninhydrin reagent comprising 2% glucose w/v provided a peak height of 97 mAU, at a reaction temperature of 131° C.

In the absence of ethylene glycol, the ninhydrin reagent comprising 2% glucose w/v provided a peak height of 79 mAU at a reaction temperature of 133° C.

The above results show a large increase in activity from glucose to sodium formate to fructose as shown by the percentage concentration required for glucose and fructose to achieve similar sensitivities which varies from 2% to 0.2% w/v respectively. The percentage concentration required for achieving the desired sensitivity is therefore expected to vary depending upon the compound(s) used to form the temperature-dependent reducing agent. Optimisation of factors such as the percentage concentration of the temperature-dependent reducing agent, percentage concentration of organic solvent if any, and the temperature of the reaction chamber, during use on standard amino acid analysers, will identify the optimal percentage concentration for all compounds passing Protocol 1 and 2.

Further, the results show that in the absence of an organic solvent the sensitivities of the temperature-dependent reducing agents decreases. However, it can be seen that this decrease in activity does not significantly affect the sensitivity of the analytical method.

The invention claimed is:

1. A ninhydrin reagent for use in a method for analysing nitrogen-containing compounds, the ninhydrin reagent comprising:
    ninhydrin;
    an aqueous buffer, wherein the ninhydrin reagent has a pH, and wherein the buffer maintains the pH at a value between 4.5 to 5.5; and
    a temperature-dependent reducing agent, which agent is inactive in the reduction of ninhydrin at a first temperature, wherein the first temperature is no greater than 30° C., and active in reducing ninhydrin to hydrindantin at a second temperature, wherein the second temperature is higher than the first temperature, further wherein the second temperature is at least 100° C.; and
    wherein the ninhydrin reagent is essentially free from hydrindantin.

2. The ninhydrin reagent according to claim 1, wherein the first temperature is from 10° C. to 20° C.

3. The ninhydrin reagent according to claim 1, wherein the temperature-dependent reducing agent is a compound having an activity of at least 50% of its initial activity after 24 months.

4. The ninhydrin reagent according to claim 1, wherein the temperature-dependent reducing agent comprises one or more saccharides.

5. The ninhydrin reagent according to claim 4, wherein the temperature-dependent reducing agent is selected from the group consisting of: Glucose, Fructose, Glyceraldehyde, Galactose, Ribose, Xylose, Erythrose, Threose, Lyxose, Arabinose, Allose, Altrose, Mannose, Gulose, Idose, Talose and L-Glycero-D-manno-heptose, Dihydroxyacetone, Erythrulose, Ribulose, Xylulose, Psicose, Sorbose, Tagatose, Sedoheptalose, or a mixture thereof; Lactose, Maltose, Trihalose, Cellobiose, Kojibiose, Nigerose, Isomaltose, Sophorose, Laminaribiose, Gentiobiose, Turanose, Maltulose, Palatinose, Gentiobiulose, Mannobiose, Melibiose, Melibiulose, Rutinose, Xylobiose or a mixture thereof; and Stachyose, Dextrin, Maltodextrin, or a mixture thereof.

6. The ninhydrin reagent according to claim 1, wherein the temperature-dependent reducing agent comprises one or more carboxylic acids and/or a salt thereof.

7. The ninhydrin reagent according to claim 6, wherein the temperature-dependent reducing agent comprises a Group I or Group II metal salt of a carboxylic acid.

8. The ninhydrin reagent according to claim 6, wherein the carboxylic acid is formic acid or a salt thereof.

9. The ninhydrin reagent according to claim 1, wherein the temperature-dependent reducing agent comprises one or more compounds having one or more aldehyde and/or ketone groups.

10. The method according to claim 9, wherein the temperature-dependent reducing agent comprises acetone.

11. The ninhydrin reagent according to claim 1, wherein the temperature-dependent reducing agent comprises a sulfite, thiosulfate, a phosphite and/or a hypophosphite.

12. The ninhydrin reagent according to claim 1, wherein the concentration of the temperature-dependent reducing agent is from 0.01% to 20% w/v or v/v.

13. The ninhydrin reagent according to claim 1, wherein the concentration of ninhydrin in the ninhydrin reagent is from 1 to 2.5% w/v or v/v.

14. The ninhydrin reagent according to claim 1, wherein the buffer comprises acetic acid, ethanoic acid or propanoic acid.

15. The ninhydrin reagent according to claim 1, further comprising one or more organic solvents.

16. The ninhydrin reagent according to claim 15, wherein the organic solvent is selected from the group consisting of dimethylsulfoxide, ethylene glycol, propylene glycol, sulfolane, carbitol, propylene glycol monomethyl ether, methylcellosolve and methanol.

17. The ninhydrin reagent according to claim 15, wherein the concentration of organic solvent is from 35% to 55% v/v.

18. A method of analysing a nitrogen-containing compound, the method comprising:
    i) providing a ninhydrin reagent according to claim 1;
    ii) heating the ninhydrin reagent to at least the second temperature to form a hydrindantin-containing mixture; and
    iii) contacting the hydrindantin-containing mixture with the nitrogen-containing compound to produce a product.

19. The method according to claim 18, wherein the product of step (iii) has a colour, the method further comprising analysing the colour of the product of step (iii).

* * * * *